United States Patent [19]
Vaughan et al.

[11] Patent Number: 5,863,853
[45] Date of Patent: Jan. 26, 1999

[54] POLYMERIZATION CATALYST SYSTEMS, THEIR PRODUCTION AND USE

[75] Inventors: George Alan Vaughan, Houston; Anthony Nicholas Speca, Kingwood; Patrick Brant, Seabrook; Jo Ann Marie Canich, Webster, all of Tex.

[73] Assignee: Exxon Chemical Patents, Inc., Houston, Tex.

[21] Appl. No.: 804,596

[22] Filed: Feb. 24, 1997

Related U.S. Application Data

[63] Continuation of Ser. No. 634,522, Apr. 18, 1996, abandoned, which is a continuation of Ser. No. 466,547, Jun. 6, 1995, abandoned, which is a continuation of Ser. No. 412,810, Mar. 29, 1995, abandoned, which is a continuation-in-part of Ser. No. 265,533, Jun. 24, 1994, abandoned.

[51] Int. Cl.$^6$ ..................................................... C08F 4/64
[52] U.S. Cl. .......................... 502/108; 502/104; 502/110; 502/113; 502/152; 526/127; 526/160; 526/161; 526/943
[58] Field of Search ..................................... 502/104, 108, 502/110, 113, 152; 526/160, 127, 161, 943

[56] References Cited

U.S. PATENT DOCUMENTS

| | | | |
|---|---|---|---|
| 4,048,423 | 9/1977 | MacLeay et al. | 526/209 |
| 4,530,914 | 7/1985 | Ewen et al. | 502/113 |
| 4,668,823 | 5/1987 | Murray | 568/17 |
| 4,939,217 | 7/1990 | Stricklen | 526/114 |
| 5,017,714 | 5/1991 | Welborn, Jr. | 556/12 |
| 5,057,475 | 10/1991 | Canich et al. | 502/104 |
| 5,240,894 | 8/1993 | Barkhardt et al. | 502/108 |
| 5,274,167 | 12/1993 | Lange et al. | 560/40 |
| 5,332,706 | 7/1994 | Nowlin et al. | 502/107 |
| 5,602,067 | 2/1997 | Nowlin et al. | 502/104 |

FOREIGN PATENT DOCUMENTS

| | | |
|---|---|---|
| 0 367 597 | 5/1990 | European Pat. Off. . |
| 589638 | 3/1994 | European Pat. Off. . |
| WO94/14855 | 7/1994 | European Pat. Off. . |
| WO95/26372 | 10/1995 | European Pat. Off. . |
| 96/14155 | 5/1996 | WIPO . |

*Primary Examiner*—David W. Wu
*Attorney, Agent, or Firm*—Paige Schmidt

[57] ABSTRACT

This invention is generally directed toward a supported catalyst system useful for polymerizing olefins. The method for supporting the catalyst system of the invention provides for a supported bulky ligand transition metal catalyst system which when utilized in a polymerization process substantially reduces the reactor fouling and sheeting particularly in a gas phase polymerization process.

18 Claims, No Drawings

POLYMERIZATION CATALYST SYSTEMS, THEIR PRODUCTION AND USE

This is a continuation, of application Ser. No. 08/634,522, filed Apr. 18, 1996 now abandoned which is a continuation of application Ser. No. 08/466,547, filed Jun. 6, 1995, now abandoned which is a continuation of application Ser. No. 08/412,810, filed Mar. 29, 1995, now abandoned which is a continuation-in-part of application Ser. No. 08/265,533, filed Jun. 24, 1994, now abandoned.

FIELD OF THE INVENTION

This invention relates to catalyst systems and to methods for their production and use in olefin polymerization. The invention particularly relates to a process for preparing a supported catalyst system for use in the gas phase, slurry phase or liquid/solution phase with improved reactor operability.

BACKGROUND OF THE INVENTION

It is desirable in many polymerization processes, particularly a slurry phase or gas phase process, to use a supported catalyst system. Generally these catalyst systems include a metallocene and alumoxane supported on a carrier, such as silica. For example, U.S. Pat. No. 4,937,217 generally describes a mixture of trimethylaluminum and triethylaluminum added to an undehydrated silica to which a metallocene catalyst component is then added. EP-308177-B1 generally describes adding a wet monomer to a reactor containing a metallocene, trialkylaluminum and undehydrated silica. U.S. Pat. Nos. 4,912,075, 4,935,397 and 4,937,301 generally relate to adding trimethylaluminum to an undehydrated silica and then adding a metallocene to form a dry supported catalyst system. U.S. Pat. No. 4,914,253 describes adding trimethylaluminum to undehydrated silica, adding a metallocene and then drying the resulting supported catalyst system with an amount of hydrogen to produce a polyethylene wax. U.S. Pat. Nos. 5,008,228, 5,086,025 and 5,147,949 generally describe forming a dry supported catalyst system by the addition of trimethylaluminum to a water impregnated silica to form alumoxane in situ and then adding the metallocene. U.S. Pat. Nos. 4,808,561, 4,897,455 and 4,701,432 describe techniques to form a supported catalyst where the inert carrier, typically silica, is calcined and contacted with a metallocene(s) and an activator/cocatalyst component. U.S. Pat. No. 5,238,892 describes forming a dry supported catalyst system by mixing a metallocene with an alkyl aluminum and then adding undehydrated silica. U.S. Pat. No. 5,240,894 generally pertains to forming a supported metallocene/alumoxane catalyst system by forming a metallocene/alumoxane reaction solution, adding a porous carrier, and evaporating the resulting slurry to remove residual solvent from the carrier.

While all these supported catalysts are useful, it would be desirable to have an improved metallocene catalyst system which in producing polymers does not foul the reactor. Particularly in a slurry or gas phase polymerization process, using these catalyst systems, there is a tendency for reactor operation problems during polymerization. During a typical polymerization process fines within the reactor often accumulate and cling or stick to the walls of a reactor. This phenomenon is often referred to as "sheeting". The accumulation of polymer particles on the reactor surfaces/walls, the recycling lines, distributor plate if employed and cooling system results in many problems including poor heat transfer during the polymerization process. Polymer particles that adhere to the walls of the reactor can continue to polymerize and often fuse together and form chunks, which can be detrimental to a continuous and batch polymerization processes.

It would be highly desirable to have an improved polymerization catalyst system that in a polymerization process would significantly enhance reactor operability and provide an improved polymer product.

SUMMARY OF THE INVENTION

This invention is generally directed towards a new supported polymerization catalyst system, to methods for its manufacture and to its use in a polymerization process.

In one embodiment an improved method is provided to produce a supported bulky ligand transition metal catalyst system by contacting a porous support with a solution comprising a metallocene catalyst component, the total volume of the metallocene solution being less than about four times the total pore volume of the porous support, preferably less than the amount at which a slurry is formed.

In another embodiment a method is provided to produce a supported bulky ligand transition metal catalyst system by contacting a porous support with a metallocene and an activator solution, wherein the total volume of the metallocene and the activator solution is less than about four times the total pore volume of the porous support, preferably less than the amount at which a slurry is formed.

In another embodiment a method is provided to produce a metallocene catalyst system by contacting a porous support with an activator solution wherein the total volume of the activator solution is greater than one times the total pore volume of the porous support but less than that amount required to form a slurry of the solution and support.

In yet another embodiment of the invention, there is provided a process for producing polyolefins by contacting olefin monomer, optionally with comonomer in the presence of the catalyst systems described above.

In yet another embodiment there is provided a catalyst system produced by the improved method.

DETAILED DESCRIPTION OF THE INVENTION

Introduction

This invention is generally directed toward a supported catalyst system useful for polymerizing olefins. The method for forming the catalyst system of the invention involves supporting a metallocene catalyst component or compound with an activator or a cocatalyst.

It has been discovered that in forming the supported catalyst system of the invention catalyst activity is maintained and in many instances increased when the volume of a metallocene and an activator solution is less than four times the pore volume of a porous support, preferably between an amount less than that required to form a slurry and above one times the total pore volume of the porous support. Making the catalyst system of the invention this way results in a simple, commercially useful and cost effective supported catalyst system with a reduced tendency for sheeting or fouling in a polymerization reactor. Also, the catalyst system of this invention results in a high bulk density polymer product having improved physical properties.

Catalyst Components of the Invention

Metallocene catalyst components, for example, are typically those bulky ligand transition metal compounds derivable from the formula:

$[L]_mM[A]_n$ where L is a bulky ligand; A is leaving group, M is a transition metal and m and n are such that the total ligand valency corresponds to the transition metal valency. Preferably the catalyst is four co-ordinate such that the compound is ionizable to a 1⁺ charge state.

The ligands L and A may be bridged to each other, and if two ligands L and/or A are present, they may be bridged. The metallocene compound may be full-sandwich compounds having two or more ligands L which may be cyclopentadienyl ligands or cyclopentadiene derived ligands or half-sandwich compounds having one ligand L, which is a cyclopentadienyl ligand or derived ligand.

The metallocene compounds contain a multiplicity of bonded atoms, preferably carbon atoms, and typically contain a cyclic structure such as, for example, a cyclopentadienyl ligand, substituted or unsubstituted, or cyclopentadienyl derived ligand or any other ligand capable of η-5 bonding to the transition metal atom. One or more bulky ligands may be π-bonded to the transition metal atom. The transition metal atom may be a Group 4, 5 or 6 transition metal and/or a metal from the lanthanide and actinide series. Other ligands may be bonded to the transition metal, such as a leaving group, such as but not limited to hydrocarbyl, hydrogen or any other univalent anionic ligand. Non-limiting examples of metallocene components and catalyst systems are discussed in for example, U.S. Pat. Nos. 4,530,914, 4,952,716, 5,124,418, 4,808,561, 4,897,455, 5,278,119, 5,304,614 all of which are herein fully incorporated by reference. Also, the disclosures of EP-A-0129,368, EP-A-0520732, EP-A-0420436, WO 91/04257 WO 92/00333, WO 93/08221, and WO 93/08199 are all fully incorporated herein by reference.

Various forms of the catalyst system of the metallocene type may be used in the polymerization process of this invention. Exemplary of the development of metallocene catalysts in the art for the polymerization of ethylene is the disclosure of U.S. Pat. No. 4,871,705 to Hoel, U.S. Pat. No. 4,937,299 to Ewen, et al., 5,324,800 (U.S. application Ser. No. 07/752,415, filed Aug. 30, 1991) and EP-A-0 129 368 published July 26, 1989, and U.S. Pat. Nos. 5,017,714 and 5,120,867 to Welborn, Jr. all of which are fully incorporated herein by reference. These publications teach the structure of the metallocene catalysts and include alumoxane as the cocatalyst. There are a variety of methods for preparing alumoxane, non-limiting examples of which are described in U.S. Pat. No. 4,665,208, 4,952,540, 5,091,352, 5,206,199, 5,204,419, 4,874,734, 4,924,018, 4,908,463, 4,968,827, 5,308,815, 5,248,801, 5,235,081, 5,157,137, 5,103,031 and EP-A-0 561 476, EP-B1-0 279 586, EP-A-0 594-218 and WO 94/10180, all of which incorporated herein by reference.

Further, the metallocene catalyst component of the invention can be a monocyclopentadienyl heteroatom containing compound. This heteroatom is activated by either an alumoxane, an ionizing activator, a Lewis acid or a combination thereof to form an active polymerization catalyst system. These types of catalyst systems are described in, for example, PCT International Publication WO 92/00333, WO 94/07928, and WO 91/04257, WO 94/03506, U.S. Pat. Nos. 5,057,475, 5,096,867, 5,055,438, 5,198,401, 5,227,440 and 5,264,405 and EP-A-0 420 436, all of which are fully incorporated herein by reference. In addition, the metallocene catalysts useful in this invention can include non-cyclopentadienyl catalyst components, or ancillary ligands such as boroles or carbollides in combination with a transition metal. Additionally it is not beyond the scope of this invention that the catalysts and catalyst systems may be those described in U.S. Pat. Nos. 5,064,802, 5,149,819, 5,243,001, 5,239,022, 5,276,208, 5,296,434, 5,321,106 and 5,304,614, PCT publications WO 93/08221 and WO 93/08199 and EP-A-0 578 838 all of which are herein incorporated by reference.

The preferred transition metal component of the catalyst system of the invention are those of Group 4, particularly, zirconium, titanium and hafnium. The transition metal may be in any oxidation state, preferably +3 or +4 or a mixture thereof. All the catalyst systems of the invention may be, optionally, prepolymerized or used in conjunction with an additive or scavenging component to enhance catalytic productivity, see for example PCT publication WO 94/07927 incorporated herein by reference.

For the purposes of this patent specification the term "metallocene" is defined to contain one or more unsubstituted or substituted cyclopentadienyl or cyclopentadienyl moiety in combination with a transition metal. In one embodiment the metallocene catalyst component is represented by the general formula $(C_p)_mMeR_nR'_p$ wherein at least one $C_p$ is an unsubstituted or, preferably, a substituted cyclopentadienyl ring symmetrical or unsymetrically substituted; Me is a Group 4, 5 or 6 transition metal; R and R' are independently selected halogen, hydrocarbyl group, or hydrocarboxyl groups having 1–20 carbon atoms or combinations thereof; m=1-3, n=0-3, p=0-3, and the sum of m+n+p equals the oxidation state of Me.

In another embodiment the metallocene catalyst component is represented by the formulas:

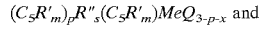 and

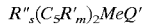

wherein Me is a Group 4, 5, 6 transition metal, at least one $C_5R'_m$ is a substituted cyclopentadienyl, each R', which can be the same or different is hydrogen, alkyl, alkenyl, aryl, alkylaryl or arylalkyl radical having from 1 to 20 carbon atoms or two carbon atoms joined together to form a part of a substituted or unsubstituted ring or rings having 4 to 20 carbon atoms, R" is one or more of or a combination of a carbon, a germanium, a silicon, a phosphorous or a nitrogen atom containing radical bridging two $(C_5R'_m)$ rings, or bridging one $(C_5R'm)$ ring back to Me, when p=0 and x=1 otherwise "x" is always equal to 0, each Q which can be the same or different is an aryl, alkyl, alkenyl, alkylaryl, or arylalkyl radical having from 1 to 20 carbon atoms, halogen, or alkoxides, Q' is an alkylidene radical having from 1–20 carbon atoms, s is 0 or 1 and when s is 0, m is 5 and p is 0, 1 or 2 and when s is 1, m is 4 and p is 1.

For the purposes of this patent specification, the terms "cocatalysts" and "activators" are used interchangeably and are defined to be any compound or component which can activate a bulky ligand transition metal compound or a metallocene, as defined above. It is within the scope of this invention to use alumoxane as an activator. There are a variety of methods for preparing alumoxane, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031 and EP-A-0 561 476, EP-B1-0 279 586, EP-A-0 594-218 and WO 94/10180, all of which are fully incorporated herein by reference. It may be preferable to use a visually clear methylalumoxane. A cloudy or gelled alumoxane can be filtered to produce a clear solution or clear alumoxane can be decanted from the cloudy solution.

It is also within the scope of this invention to use ionizing activators, neutral or ionic, or compounds such as tri (n-butyl) ammonium tetrakis(pentaflurophenyl) boron, which ionize the neutral metallocene compound. Such ionizing compounds may contain an active proton, or some other cation associated with but not coordinated or only loosely coordinated to the remaining ion of the ionizing compound. Combinations of activators are also contemplated by the invention, for example, alumoxane and ionizing activators in combinations, see for example, WO 94/07928.

Descriptions of ionic catalysts for coordination polymerization comprised of metallocene cations activated by non-coordinating anions appear in the early work in EP-A-0 277 003, EP-A-0 277 004 and U.S. Pat. No. 5,198,401 and WO-A-92/00333 (incorporated herein by reference). These teach a preferred method of preparation wherein metallocenes (bis$C_p$ and mono$C_p$) are protonated by an anion precursor such that an alkyl/hydride group is abstracted from a transition metal to make it both cationic and charge-balanced by the non-coordinating anion.

The term "noncoordinating anion" means an anion which either does not coordinate to said cation or which is only weakly coordinated to said cation thereby remaining sufficiently labile to be displaced by a neutral Lewis base. "Compatible" noncoordinating anions are those which are not degraded to neutrality when the initially formed complex decomposes. Further, the anion will not transfer an anionic substituent or fragment to the cation so as to cause it to form a neutral four coordinate metallocene compound and a neutral by-product from the anion. Noncoordinating anions useful in accordance with this invention are those which are compatible, stabilize the metallocene cation in the sense of balancing its ionic charge in a +1 state, yet retain sufficient lability to permit displacement by an ethylenically or acetylenically unsaturated monomer during polymerization.

The use of ionizing ionic compounds not containing an active proton but capable of producing the both the active metallocene cation and an noncoordinating anion is also known. See, EP-A-0 426 637 and EP-A-0 573 403 (incorporated herein by reference). An additional method of making the ionic catalysts uses ionizing anion pre-cursors which are initially neutral Lewis acids but form the cation and anion upon ionizing reaction with the metallocene compounds, for example the use of tris(pentafluorophenyl) boron. See EP-A-0 520 732 (incorporated herein by reference). Ionic catalysts for addition polymerization can also be prepared by oxidation of the metal centers of transition metal compounds by anion pre-cursors containing metallic oxidizing groups along with the anion groups, see EP-A-0 495 375 (incorporated herein by reference).

Where the metal ligands include halogen moieties (for example, bis-cyclopentadienyl zirconium dichloride) which are not capable of ionizing abstraction under standard conditions, they can be converted via known alkylation reactions with organometallic compounds such as lithium or aluminum hydrides or alkyls, alkylalumoxanes, Grignard reagents, etc. See EP-A-0 500 944 and EP-A1-0 570 982 (incorporated herein by reference) for in situ processes describing the reaction of alkyl aluminum compounds with dihalo-substituted metallocene compounds prior to or with the addition of activating anionic compounds.

Methods of supporting ionic catalysts comprising metallocene cations and noncoordinating anions are described in WO 91/09882, WO 94/03506 and in co-pending U.S. Ser. No. 08/248,284, filed Aug. 3 1994 now abandoned (incorporated herein by reference). The methods generally comprise either physical adsorption on traditional polymeric or inorganic supports that have been largely dehydrated and dehydroxylated, or using neutral anion precursors that are sufficiently strong Lewis acids to activate retained hydroxy groups in silica containing inorganic oxide supports such that the Lewis acid becomes covalently bound and the hydrogen of the hydroxy group is available to protonate the metallocene compounds.

For purposes of this patent specification the terms "carrier" or "support" are interchangeable and can be any support material, preferably a porous support material, such as for example, talc, inorganic oxides, inorganic chlorides, for example magnesium chloride and resinous support materials such as polystyrene polyolefin or polymeric compounds or any other organic support material and the like that has an average particle size greater than 10 $\mu$m.

The preferred support materials are inorganic oxide materials, which include those from the Periodic Table of Elements of Groups 2, 3, 4, 5, 13 or 14 metal oxides. In a preferred embodiment, the catalyst support materials include silica, alumina, silica-alumina, and mixtures thereof. Other inorganic oxides that may be employed either alone or in combination with the silica, alumina or silica-alumina are magnesia, titania, zirconia, and the like.

It is preferred that the carrier of the catalyst of this invention has a surface area in the range of from about 10 to about 700 $m^2/g$, pore volume in the range of from about 0.1 to about 4.0 cc/g and average particle size in the range of from about 10 to about 500 $\mu$m. More preferably, the surface area is in the range of from about 50 to about 500 $m^2/g$, pore volume of from about 0.5 to about 3.5 cc/g and average particle size of from about 20 to about 200 $\mu$m. Most preferably the surface area range is from about 100 to about 400 $m^2/g$, pore volume from about 0.8 to about 3.0 cc/g and average particle size is from about 30 to about 100 $\mu$m. The pore size of the carrier of the invention typically has pore size in the range of from 10 to 1000° Å, preferably 50 to about 500° Å, and most preferably 75 to about 350° Å.

Method of Producing the Catalyst System of the Invention

The supported catalyst system of the invention can be made in a variety of different ways.

For the purposes of this patent specification and appended claims the term "solution" includes a suspension, a slurry or a mixture. Any compatible solvent or other liquid capable of forming a solution or the like with at least one metallocene catalyst component and/or at least one activator of the invention can be used. Non-limiting examples of solvents are those aliphatic, aromatic and saturated hydrocarbons and cyclic hydrocarbons, such as isopentane, heptane, toluene and the like. The more preferred solvents are the cyclic aliphatic and aromatic hydrocarbons, the most preferred of which is toluene.

In one embodiment, the metallocene catalyst component is typically slurried in a solvent to form a metallocene solution and a separate solution is formed containing an activator and a solvent. The metallocene solution and the activator solution are then added to a porous support, or vice-versa, or any combination thereof.

In another embodiment, the metallocene solution is added to the porous support first before the addition of the activator solution. In yet another embodiment, the activator solution is added first to the porous support, or vice versa, before the addition of the metallocene solution. In still yet another embodiment, part or all of the metallocene solution can be added to the porous support material, or vice-versa, followed by the addition of all or part of the activator solution. If parts are used the remaining portions of each solution can be added in any order to the porous support.

It is preferable to apply the solution containing catalyst component(s) to the support such that a homogeneous catalyst system is obtained, i.e., wherein the component(s) are evenly distributed on and within the support material particles. In a preferred embodiment, the total volume of solution containing metallocene and activator added to the support is in the range of from less than that volume at which a slurry is formed to above that volume equal to the total pore volume of the support, preferably from 2.5 times the total pore volume of the support to about 1.05 times the total pore volume of the support, more preferably from about 2.4 to about 1.1 times the total pore volume of the support, even more preferably from about 2.3 to about 1.2 times the total pore volume of the suppport, even more preferably from about 2.2 to about 1.25 times the total pore volume of the support, even more preferably from about 2.1 to about 1.27 times the total pore volume of the support, even more preferably from about 2.0 to about 1.3 times the total pore volume of the support, and even more preferably from about 2.0 to about 1.5 times the total pore volume of the support. Preferably, the solution is applied either dropwise or as a spray while the support is agitated or otherwise thoroughly mixed.

Generally, a slurry is formed when two phases are observable one of which contains all or most of the support material. The volume of solution required to reach this stage will vary depending upon among other things the type of support material and type of catalyst system components. Just prior to the point at which a slurry is formed, is a stage which is defined herein as the "mud" stage. At the mud stage, the solution volume is such that, while two phases are not visible, the support material is saturated and the support particles are firmly packed together. Prior to the mud stage, the volume of solution is such that the support material appearance ranges from dry and free flowing (even though the support may contain close to one pore volume of solution) to dry but slightly sticky to variously damp and clumpy such as is the appearance of variously wet sand.

In one embodiment, the volume of solution applied to the support material ranges from above one pore volume to that required to form a slurry, preferably from above one pore volume to that required to reach the mud stage. It should be recognized that catalyst systems formed in the mud stage are more difficult to mix and require longer drying times as compared to those prepared with less solution. Below one pore volume it may be difficult to obtain homogeneous coverage of the support material with the catalyst system components. This may lead to fouling.

In the most preferred embodiment, the metallocene and the activator are combined to form a solution which is then added to a porous support.

The catalyst systems of the invention can be used in slurry form or dried to a free-flowing powder. As a free flowing powder the catalyst system of the invention can still contain an amount of solvent, for example, toluene, in the support's pores, however, it is preferred that substantially all the solvent is removed. For purposes of this specification and appended claims the term "substantially all the solvent is removed" means that greater than about 90% of all the solvent is removed from the supported catalyst system when drying.

In another embodiment, the dried supported catalyst system is washed or otherwise treated to remove weakly associated catalyst component(s). Any hydrocarbon may be used to wash the catalyst system, however, the hydrocarbon should be capable of dissolving the catalyst component and should be easy to dry from the support. Toluene and hexane are preferred.

It is within the scope of the invention to separately support at least one metallocene on one porous support and support at least one activator on another porous support wherein the total volume of the metallocene solution on the first porous support and the total volume of activator solution is as described above.

The procedure for measuring the total pore volume of a porous support is well known in the art. Details of one of these procedures is discussed in Volume 1, *Experimental Methods in Catalytic Research* (Academic Press, 1968) (specifically see pages 67–96). This preferred procedure involves the use of a classical BET apparatus for nitrogen absorption. Another method well know in the art is described in Innes, *Total porosity and Particle Density of Fluid Catalysts By Liquid Titration*, Vol. 28, No. 3, Analytical Chemistry 332–334 (March, 1956).

In another embodiment of the invention, the mole ratio of the metal of the activator component to the transition metal of the metallocene component is in the range of ratios between 0.3:1 to 1000:1, preferably 20:1 to 800:1, and most preferably 50:1 to 500:1.

In another embodiment where the activator is an ionizing activator as previously described the mole ratio of the metal of the activator component to the transition metal component is in the range of ratios between 0.3:1 to 3:1.

The supported catalyst system of the invention may include a surface modifier such as that described in U.S. patent application No. 08/322,675 now abandoned (fully incorporated herein by reference) and/or an antistatic agent, for example, those described in U.S. Pat. No. 5,283,278, fully incorporated herein by reference. Non-limiting examples of antistatic agents include, alcohol, thiol, silanol, diol, ester, ketone, aldehyde, acid, amine, and ether compounds. Tertiary amine compounds are preferred. The antistatic agent can be added at any stage in the formation of the supported catalyst system of the invention, however, it is preferred that it is added after the supported catalyst system of the invention is formed, in either a slurry or dried state.

In another embodiment of the invention, the supported catalyst system of the invention includes a polyolefin wax or tackifier or the like.

Polymerization Process of the Invention

The catalyst system of this invention is suited for the polymerization of monomers and optionally comonomers in any polymerization or prepolymerization process, gas, slurry or solution phase; even a high pressure autoclave process can be utilized. In the preferred embodiment a gas phase or slurry phase process is utilized, most preferably a gas phase process is used.

In the preferred embodiment, this invention is directed toward the slurry or gas phase polymerization or copolymerization reactions involving the polymerization or optionally prepolymerization of one or more of the alpha-olefin monomers having from 2 to 20 carbon atoms, preferably 2–12 carbon atoms. The invention is particularly well suited to the copolymerization reactions involving the polymerization of one or more of the monomers, for example alpha-olefin monomers of ethylene, propylene, butene-1, pentene-1, 4-methylpentene-1, hexene-1, octene-1, decene-1, and cyclic olefins and styrene. Other monomers can include polar vinyl, diolefins such as dienes, norbomene, norboradiene, acetylene and aldehyde monomers. Preferably a copolymer of ethylene or propylene is produced. Preferably the comonomer is an alpha-olefin having from 3 to 15 carbon atoms, preferably 4 to 12 carbon atoms and most preferably 4 to 10 carbon atoms. In another embodiment ethylene or propylene is polymerized with at least two comonomers to form a terpolymer and the like.

In one embodiment of the process of the invention, the olefin(s) are prepolymerized in the presence of the catalyst system of the invention prior to the main polymerization. The prepolymerization can be carried out batchwise or continuously in gas, solution or slurry phase including at elevated pressures. The prepolymerization can take place with any alpha-olefin monomer or combination and/or in the presence of any molecular weight controlling agent such as hydrogen. For details on prepolymerization see U.S. Pat. No. 4,923,833 and 4,921,825 and EP-B-0279 863, published Oct. 14, 1992 all of which are incorporated fully herein by reference. All the catalyst systems of the invention may be optionally prepolymerized or used in conjunction with an additive or scavenging component to enhance catalytic productivity.

Typically in a gas phase polymerization process a continuous cycle is employed where in one part of the cycle of a reactor, a cycling gas stream, otherwise known as a recycle stream or fluidizing medium, is heated in the reactor by the heat of polymerization. This heat is removed in another part of the cycle by a cooling system external to the reactor. (See for example U.S. Pat. Nos. 4,543,399, 4,588,790, 5,028,670 and 5,352,749 and WO 94/28032 published Dec. 8, 1994 all of which are fully incorporated herein by reference.)

Generally in a gas fluidized bed process for producing polymer from monomers a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and new or fresh monomer is added to replace the polymerized monomer.

A slurry polymerization process generally uses pressures in the range of about 1 to about 500 atmospheres and even greater and temperatures in the range of −60° C. to about 280° C. In a slurry polymerization, a suspension of solid, particulate polymer is formed in a liquid polymerization medium to which ethylene and comonomers and often hydrogen along with catalyst are added. The liquid employed in the polymerization medium can be alkane or cycloalkane, or an aromatic hydrocarbon such as toluene, isobutylene, ethylbenzene or xylene. The medium employed should be liquid under the conditions of polymerization and relatively inert. Preferably, hexane or isobutane is employed.

Polymer Compositions and Applications of the Invention

MWD, or polydispersity, is a well known characteristic of polymers. MWD is generally described as the ratio of the weight average molecular weight (Mw) to the number average molecular weight (Mn). The ratio Mw/Nn can be measured directly by gel permeation chromatography techniques, or indirectly, by measuring the ratio of $I_{21}$ to $I_2$ as described in ASTM D-1238-F and ASTM D-1238-E respectively. $I_2$ is well known in the art as equivalent to Melt Index (MI). $I_{21}$ is also known as high load melt index (HLMI). MI is inversely proportional to the molecular weight of the polymer (Mw). The MI of the polymers of the invention are generally in the range of about 0.1 dg/min to about 1000 dg/min, preferably about 0.2 dg/min to about 300 dg/min, more preferably about 0.3 to about 200 dg/min and most preferably about 0.5 dg/min to about 100 dg/min.

The ratio of $I_{21}/I_2$ is known as the melt index ratio (MIR) and for the purposes of this patent specification the ratio is also defined to be melt flow ratio (MFR). MIR is generally proportional to the MWD.

The MIR of the polymers of this invention are generally in the range of greater than 10 to about 200, preferably about 12 to 60 and most preferably about 14 to about 45.

The ethylene homopolymer and copolymer compositions of the invention have a density in the range of from about 0.86 g/cm$^3$ to about 0.97 g/cm$^3$, preferably about 0.88 g/cm$^3$ to about 0.96 g/cm$^3$, more preferably between about 0.90 g/cm$^3$ to about 0.955 g/cm$^3$ and most preferably between about 0.91 g/cm$^3$ to about 0.95 g/cm$^3$.

The MWD of the polymers of the invention are in the range of greater than about 1.8 to less than about 20, preferably in the range of greater than about 2 to about 5.

Another important characteristic of the polymer of the invention is its composition distribution (CD). A measure of composition distribution is the "Composition Distribution Breadth Index" ("CDBI"). CDBI is defined as the weight percent of the copolymer molecules having a comonomer content within 50% (that is, 25% on each side) of the median total molar comonomer content. The CDBI of a copolymer is readily determined utilizing well known techniques for isolating individual fractions of a sample of the copolymer. One such technique is Temperature Rising Elution Fraction (TREF), as described in Wild, et al., *J. Poly. Sci., Poly. Phys. Ed.*, vol. 20, p. 441 (1982) and U.S. Pat. No. 5,008,204, which are incorporated herein by reference.

To determine CDBI, a solubility distribution curve is first generated for the copolymer. This may be accomplished using data acquired from the TREF technique described above. This solubility distribution curve is a plot of the weight fraction of the copolymer that is solubilized as a function of temperature. This is converted to a weight fraction versus composition distribution curve. For the purpose of simplifying the correlation of composition with elution temperature the weight fractions are assumed to have a Mn≧15,000, where Mn is the number average molecular weight fraction. Low weight fractions generally represent a trivial portion of the polymer of the present invention. The remainder of this description and the appended claims maintain this convention of assuming all weight fractions have a Mn≧15,000 in the CDBI measurement.

From the weight fraction versus composition distribution curve the CDBI is determined by establishing what weight percent of the sample has a comonomer content within 25% each side of the median comonomer content. Further details of determining the CDBI of a copolymer are known to those skilled in the art. See, for example, PCT patent application WO 93/03093, published Feb. 18, 1993.

The polymers of the present invention in one embodiment have CDBI's generally in the range of greater than 50% to 99%, preferably in the range of 50% to 85%, and more preferably 55% to 80%, even more preferably greater than 60%, still even more preferably greater than 65%. Obviously, higher or lower CDBI's may be obtained using other catalyst systems with changes in the operating conditions of the process employed.

In some instances where it is necessary to improve processability and manipulate final end product characteristics the polymers produced by this present invention can be blended or coextruded into single or muitilayer films or the like with various other polymers and compounds well known in the art, for instance, LLDPE, LDPE, high and low high density polyethylene, polypropylene, PB, EMA, EVA, copolymers of acrylic acid, polymethylacrylate or any other polymers such as polyvinyichloride, polybutene-1, isotactic polybutene, ABS resins, ethylene-propylene rubber, vulcanized ethylene-propylene rubber, EPDM block copolymer elastomers, copolymers of ethylene and vinyl alcohol, polystyrene, nylons, PET resins, crosslinked polyethylenes, poly-1-esters, graft copolymers, polyacrylonitrile homopolymers or copolymers, thermoplastic polyamides, polyacetal, polyvinylidine fluoride and other fluorinated elastomers, polyethylene glycols, polyisobutylene, terpene resins and other tackifying polymers and the like and combinations thereof In many applications it will desirable to combine the polymer of the invention with anti-oxidants, slip, anti-block, processing aids, pigments, ultra-violet inhibitors, antistatic agents, or other additives. The polymers produced by the process of the invention are useful in such forming operations as film, sheet, and fiber extrusion and co-extrusion as well as blow molding, injection molding and rotary molding. Films include blown or cast films in mono-layer or multi-layer constructions formed by coextrusion or by lamination. Such films are useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fiber forming operations include melt spinning, solution spinning and melt blown fiber operations. Such fibers may be used in woven or non-woven form to make filters, diaper fabrics, medical garments, geotextiles, etc. General extruded articles include medical tubing, wire and cable coatings, geomembranes, and pond liners. Molded articles include single and multi-layered constructions in the form of bottles, tanks, large hollow articles, rigid food containers and toys, etc.

EXAMPLES

In order to provide a better understanding of the present invention including representative advantages and limitations thereof, the following examples are offered.

Density is measured in accordance with ASTM-D-1238. The ratio of Mw/Mn can be measured directly by gel permeation chromatography techniques. For the purposes of this patent specification the MWD of a polymer is determined with a Waters Gel Permeation Chromatograph equipped with Ultrastyrogel columns and a refractive index detector. In this development, the operating temperature of the instrument was set at 145° C., the eluting solvent was trichlorobenzene, and the calibration standards included sixteen polystyrenes of precisely known molecular weight, ranging from a molecular weight of 500 to a molecular weight of 5.2 million, and a polyethylene standard, NBS 1475. In all examples the supernatant of a 30 weight percent methyl alumoxane in toluene available from Ethyl Corporation, Baton Rouge, Louisiana was used, otherwise known in the art as clear methylalumoxane.

Example 1
Method 1

The alumoxane in toluene is combined with the metallocene to produce a precursor solution. The silica is charged to a glass vessel and the precursor solution is added intermittently in small aliquots. Between additions the vessel is sealed and the silica—precursor mixture is agitated by vigorous shaking. The total volume of precursor added does not exceed the total available silica pore volume and the mixture is always composed of finely divided particles and free-flowing. In this way the precursor becomes incorporated into the pores of the silica uniformly. The toluene can be removed in vacuo until no further weight loss occurs.
Catalyst 1-1

A precursor was prepared by combining 19.61 g of 30 wt % methyl aluminoxane in toluene (82.37 millimoles Al) and 0.548 g of bis(1-butyl-3-methylcyclopentadienyl)zirconium dichloride (1.27 millimoles Zr) with stirring. In accordance with Method 1, 2.04 g of the precursor was added to 2.182 g of silica (MS948, 1.6 cc/g P.V., W. R. Grace, Davison Chemical Division, Baltimore, Md. (Davison Chemical Co.) previously heated to 800° C. under $N_2$. The ratio of liquid volume to total silica pore volume was 0.63. The finely divided, free-flowing solid was dried at reduced pressure (28+ in. Hg vacuum) and 40° C. for 4 hours. 3.10 g catalyst was obtained. Elemental analysis showed 0.38 wt % Zr and 8.87 wt % Al.
Catalyst 1-2

A precursor solution was prepared by combining 30.27 g of 30 wt % methyl aluminoxane in toluene (127.13 millimoles Al) and 0.556 g of bis(I-butyl-3-methylcyclopentadienyl)zirconium dichloride (1.29 millimoles Zr) with stirring. In accordance with Method 1, 4.205 g of the precursor was added to 2.982 g of silica (MS948, 1.6 cc/g P.V.), (Davison Chemical Co.) previously heated to 800° C. under $N_2$. The ratio of liquid volume to total silica pore volume was 0.95. The finely divided, free-flowing solid was dried at reduced pressure (28+ in. Hg vacuum) and 40° C. for 4 hours. Elemental analysis showed 0.39 wt % Zr and 12.93 wt % Al.
Catalyst 1-3

A precursor was prepared by combining 7.25 g of 30 wt. % aluminoxane in toluene (0.037 mol) with 1.09 g of toluene and 0.153 g of bis(1-butyl-3-methylcyclopentadienyl) zirconium dichloride (0.35 mmol) with stirring. In accordance with Method 1, the precursor was added to 6.004 g of silica (MS948, 1.6 cc/g P.V., Davison Chemical Co) previously heated to 800° C. under $N_2$. The ratio of liquid volume to total silica pore volume was 0.91. The solid was completely free flowing and was dried at reduced pressure (28+ in. Hg) and 25° C. for 16 hours.
Catalyst 1-4

A precursor was prepared by combining 7.25 g of 30 wt. % aluminoxane in toluene (0.037 mol) with 0.153 g of bis(1-butyl-3-methylcyclopentadienyl)zirconium dichloride (0.35 mmol) and no added toluene with stirring. In accordance with Method 1, the precursor was added to 6.002 g of silica (MS948, 1.6 cc/g P.V., Davison Chemical Co) previously heated to 800° C. under $N_2$. The ratio of liquid volume to total silica pore volume was 0.79. The solid was completely free flowing and was dried at reduced pressure (28+ in. Hg) and 25° C. for 16 hours.

Example 2
Method 2

The aluminoxane in toluene is combined with the metallocene to produce a precursor solution. The silica is charged to a vessel equipped with an agitator made up of numerous wire loops. The agitator rotates and passes through the total volume of the vessel. The precursor solution is added dropwise. The total volume of precursor added does not exceed the total silica pore volume, and the mixture is always composed of finely divided particles and free-flowing. In this way the precursor becomes incorporated into the pores of the silica uniformly. The toluene is removed in vacuo until no further weight loss occurs.
Catalyst 2-1 and 2-2

A precursor solution was prepared by combining 130.0 g of 30 wt % methyl aluminoxane in toluene solution (0.669 moles Al) and 4.46 g of bis(1-butyl-3-methylcyclopentadienyl)zirconium dichloride (10.3 millimoles Zr) with stirring. In accordance with Method 2, the precursor was added to 150 g of silica (MS948, 1.6 cc/g P.V.), (Davison Chemical Co.) previously heated to 800° C. under $N_2$. The ratio of liquid volume to total silica pore volume was 0.60. About one-third of the finely divided, free-flowing catalyst was dried at reduced pressure (25.4 in Hg vacuum) and 25° C. for 16 hours. 93 g catalyst was obtained. Elemental analysis showed 0.5 wt % Zr and 9.65 wt % Al. To the remaining two-thirds of the finely divided, free-flowing catalyst was added a precursor containing 48.35 g of 30 wt % methyl aluminoxane in toluene (0.249 moles Al) and 1.65 g of bis(1-butyl-3-methylcyclopentadienyl)zirconium dichloride (3.81 millimoles Zr). The ratio of liquid volume to total silica pore volume was 0.88. The finely divided, free-flowing solid was dried at reduced pressure (28+ in. Hg vacuum) and 25° C. for 16 hours. 183 g catalyst was obtained. Elemental analysis showed 0.7 wt % Zr and 13.03 wt % Al.

Example 3

Method 3

The aluminoxane in toluene is combined with the metallocene to produce a precursor solution. The silica is charged to a vessel equipped with a multi-blade agitator capable of high speed rotation. The precursor solution is added dropwise. The total volume of precursor added does not exceed the total available silica pore volume and the mixture is always composed of finely divided particles and free-flowing. In this way the precursor becomes incorporated into the pores of the silica uniformly. The toluene is removed in vacuo until no further weight loss occurs.

Catalyst 3-1 and 3-2

A precursor solution was prepared by combining 77.16 g of 30 wt % methyl aluminoxane in toluene (0.397 moles Al) and 1.56 g of bis(1-butyl-3-methylcyclopentadienyl) zirconium dichloride (3.61 millimoles Zr) with stirring. In accordance with Method 3, the precursor was added to 59.92 g of silica (MS948, 1.6 cc/g P.V., Davison Chemical Co.) previously heated to 800° C. under $N_2$. The ratio of liquid volume to total silica pore volume was 0.88. About one-half of the finely divided, free-flowing solid was dried at reduced pressure (28+ in. Hg vacuum) and 85° C. for 4 hours. 40.31 g catalyst was obtained. Elemental analysis showed 0.37 wt % Zr and 11.83 wt % Al. The remainder of the finely divided, free-flowing solid was dried at reduced pressure (28+ in. Hg vacuum) and 25° C. for 16 hours. 183 g catalyst was obtained. Elemental analysis showed 0.35 wt % Zr and 11.02 wt % Al.

Catalyst 3-3

Using the catalyst preparation vessel described in Method 3, 6.48 g of 30 wt % methyl aluminoxane in toluene (33.41 millimoles Al) was added to 10.217 g of silica (MS948, 1.6 cc/g P.V., Davison Chemical Co.) previously heated to 800° C. under $N_2$. The ratio of liquid volume to total silica pore volume was 0.43. This was followed by a solution of 0.264 g bis(1-butyl-3-methylcyclopentadienyl)zirconium dichloride (0.61 millimoles Zr) in 4.27 g toluene. Then 6.50 g of 30 wt % methyl aluminoxane in toluene (33.51 millimoles Al) was added. During the final addition, a slow $N_2$ purge was used to remove excess toluene and maintain the liquid volume to total silica pore volume to about 1. The finely divided, free-flowing solid was dried at reduced pressure (28+ in. Hg vacuum) and 40° C. for 4 hours. 18.73 g catalyst was obtained. Elemental analysis showed 0.33 wt % Zr and 11.75 wt % Al.

Catalyst 3-4

A catalyst was prepared as described above except a precursor solution of 9.77 g of 30 wt % methyl aluminoxane in toluene (50.32 millimole Al) and 0.395 g bis(1-butyl-3-methylcyclopentadienyl)zirconium dichloride (0.61 millimoles Zr) was added to 15.15 g of silica (MS948, 1.6 cc/g P.V., Davison Chemical Co.) previously heated to 800° C. under $N_2$. The ratio of liquid volume to total silica pore volume was 0.44. This was followed by 9.78 g more 30 wt % methyl aluminoxane in toluene. The ratio of liquid volume to total silica pore volume was 0.88. The finely divided, free-flowing solid was dried at reduced pressure (28+ in. Hg vacuum) and 40° C. for 4 hours. 25.46 g catalyst was obtained. Elemental analysis showed 0.35 wt % Zr and 11.37 wt % Al.

Example 4

Method 4

As in Method 2, the aluminoxane in toluene is combined with the metallocene to produce a precursor solution. The silica is charged to a vessel equipped with an agitator made up of numerous wire loops. The agitator rotates and passes through the total volume of the vessel. The silica is added rapidly to the precursor solution or vice versa. The total volume of the precursor is greater than the total available pore volume, but not more than that volume required to form a gel or slurrry. The toluene is removed in vacuo until no further weight loss occurs.

Catalyst 4-1

A precursor was prepared by combining 325 mL of 30 wt. % methyl aluminoxane in toluene (1.56 moi) with 358 g of toluene and 6.5 g of bis(1-butyl-3-methylcyclopentadienyl) zirconium dichloride (0.015 mol) with stirring. In accordance with Method 4, 250 g of silica (MS948, 1.6 cc/g pore volume (P.V.), Davison Chemical Co) previously heated to 850° C. under $N_2$ was added to the precursor. The ratio of liquid volume to total silica pore volume was 1.8. The solid was neither gelled nor completely free flowing and was dried at reduced pressure (28+ in. Hg vacuum) and 25° C. for two 16 hour periods.

Example 5

Method 5

The aluminoxane or suitable activator such as $B(C_6F_5)_3$ in toluene is combined with the metallocene to produce a precursor solution. The silica is charged to a glass vessel and the precursor solution is added all at once. Alternatively the precursor solution is charged to a glass vessel and the silica is added to the precursor all at once. The mixture is mixed thoroughly using a spatula. The total volume of the precursor is greater than the total available pore volume, but not enough to form a mixture that has reached the point of gelation or slurry. The toluene is removed in vacuo until no further weight loss occurs.

Catalyst 5-1

A precursor was prepared by combining 36.27 g of 30 wt. % methyl aluminoxane in toluene (0.184 mol) with 42.8 g of toluene and 0.781 g of bis(1-butyl-3-methylcyclopentadienyl)zirconium dichloride (1.81 mmol) with stirring. In accordance with Method 5, 30.01 g of silica (MS948, 1.6 cc/g P.V., Davison Chemical Co) previously heated to 800° C. under $N_2$ was added to the precursor. The ratio of liquid volume to total silica pore volume was 1.8. The solid was neither a slurry nor completely free flowing and was dried at reduced pressure (28+ in. Hg vacuum) and 25° C. for two 16 hour periods.

Catalyst 5-1A

A precursor was prepared by combining 36.27 g of 30 wt % methyl aluminoxane in toluene (0.184 mol) with 118 g of toluene and 0.783 g of bis(1-butyl-3-methylcyclopentadienyl)zirconium dichloride (1.81 mmol) with stirring. Next 30.01 g of silica (MS948, 1.6 cc/g P.V., Davison Chemical Co) previously heated to 800° C. under $N_2$ was added to the precursor while stirred by means of a magnetic stir bar. The ratio of liquid volume to total silica pore volume was 3.7. The slurry was dried with stirring at reduced pressure (28+ in. Hg vacuum) until it became a free flowing solid, after which stirring was ceased and drying continued at 25° C. for one 16 hour period.

Catalyst 5-2

A precursor was prepared by combining 0.205 g of $B(C_6F_5)_3$ in toluene (0.400 mmol) with 14.2 g of toluene and 0.144 g of bis(1-butyl-3-methylcyclopentadienyl)zirconium dichloride (0.333 mmol) with stirring. In accordance with Method 5, the precursor was added to 6.01 g of silica (MS948, 1.6 cc/g P.V., Davison Chemical Co) previously heated to 800° C. under $N_2$. The ratio of liquid volume to total silica pore volume was 1.3. The solid was neither a slurry nor completely free flowing and was dried at reduced pressure (28+ in. Hg vacuum) and 25° C. for one 16 hour period.

Catalyst 5-3, 5-4, and 5-5

A precursor was prepared by combining 29.06 g of 30 wt % methyl aluminoxane in toluene (0.148 mol) with 36.9 g of toluene. In accordance with Method 5, the precursor was added to 24.36 g of silica (MS948, 1.6 cc/g P.V., Davison Chemical Co) previously heated to 800° C. under $N_2$. The ratio of liquid volume to total silica pore volume was 1.5. The solid was neither a slurry nor completely free flowing and was dried at reduced pressure (28+ in. Hg vacuum) and 25° C. for one 16 hour period. The resulting solid was stirred with 300 mL of pentane and filtered. The solids were washed with a 100 mL and four 250 mL portions of pentane and then dried at reduced pressure (28+ in. Hg vacuum) and 25° C. until a constant weight was reached.

Next a second precursor was prepared by combining 0.094 g of bis(1-butyl-3-methylcyclopentadienyl)zirconium dichloride (0.217 mmol) with 10.98 g of toluene. This precursor was added to 5.001 g of the dried methyl aluminoxane/silica mixture and the resulting mixture was thoroughly, stirred with a spatula and was dried at reduced pressure (28+ in. Hg vacuum) and 25° C. for one 16 hour period.

A third precursor was prepared by combining 0.060 g of dimethylsilyl (tetramethylcyclopentadienyl) (adamantylamido)titanium dichloride (0.134 mmol) with 5.8 g of pentane and 2 g of toluene warmed to 40° C. This precursor was added to 3.012 g of the dried methyl aluminoxane/silica mixture or compound and the resulting mixture was thoroughly stirred with a spatula and was dried at reduced pressure (28+ in. Hg vacuum) and 25° C. for one 16 hour period.

A fourth precursor was prepared similarly to the third precursor using 0.031 g of dimethylsilyl (tetramethylcyclopentadienyl)(adamantylamido)titanium dichloride (0.069 mmol) and 0.055 g of bis(1-butyl-3-methylcyclopentadienyl)zirconium dichloride (0.127 mmol) with 3.5 g of pentane and 1.7 g of toluene warmed to 40° C. This precursor was added to 3.000 g of the dried methyl aluminoxane/silica mixture and the resulting mixture was thoroughly stirred with a spatula and was dried at reduced pressure (28+ in. Hg vacuum) and 25° C. until a constant weight was reached.

Catalyst 5-6

A precursor was prepared by combining 7.434 g of 30 wt % methyl aluminoxane in toluene (37.7 mmol) with 9.21 g of toluene and 0.601 g of dimethylsilyl (tetramethylcyclopentadienyl)(t-butylamido)dimethyl titanium (1.37 mmol) with stirring. In accordance with Method 5, 5.994 g of silica (MS948, 1.6 cc/g P.V., Davison Chemical Co) previously heated to 800° C. under $N_2$ was added to the precursor. The ratio of liquid volume to total silica pore volume was 1.1. The solid was neither a slurry nor completely free flowing and was dried at reduced pressure (28+ in. Hg vacuum) and 25° C. for two 16 hour periods.

Catalyst 5-7

A precursor was prepared by combining 36.27 g of 30 wt. % aluminoxane in toluene (0.184 mol) with 42.8 g of toluene and 0.781 g of bis(1-butyl-3-methylcyclopentadienyl) zirconium dichloride (1.81 mmol) with stirring. In accordance with Method 5, 30.00 g of silica (MS948, 1.6 cc/g P.V., Davison Chemical Co) previously heated to 800° C. under $N_2$ was added to the precursor. The ratio of liquid volume to total silica pore volume was 1.8. The solid was neither a slurry nor completely free flowing and was dried at reduced pressure (28+ in. Hg) and 25° C. for 16 hours.

Catalyst 5-8

A precursor was prepared by combining 7.25 g of 30 wt. % alumninoxane in toluene (0.037 mol) with 4.75 g of toluene and 0.152 g of bis(1-butyl-3-methylcyclopentadienyl)zirconium dichloride (0.35 mmol) with stirring. In accordance with Method 5, 6.009 g of silica (MS948, 1.6 cc/g P.V., Davison Chemical Co) previously heated to 800° C. under $N_2$ was added to the precursor. The ratio of liquid volume to total silica pore volume was 1.3. The solid was neither a slurry nor completely free flowing and was dried at reduced pressure (28+ in. Hg) and 25° C. for 16 hours.

Example 6

Method 6

The aluminoxane or suitable activator such as $B(C_6F_5)_3$ in toluene is combined with the metallocene to produce a precursor solution. The silica is charged to a glass vessel and the precursor solution is added with gentle stirring by a steel stirring shaft spatula or magnetic stir bar. Alternatively the precursor solution is charged to a glass vessel and the silica is added to the precursor with stirring. The initial volume of the precursor is greater than the total available pore volume, but not more than twice the total available pore volume so that the mixture does not contain free flowing solvent or reach the point of forming a slurry. A further portion of solvent less than the total pore volume is added and stirring continued. The toluene is removed in vacuo until no further weight loss occurs.

Catalyst 6-1

A precursor was prepared by combining 36.27 g of 30 wt % methyl aluminoxane in toluene (0.187 mol) with 42.2 g of toluene and 0.781 g of bis(1-butyl-3-methylcyclopentadienyl)zirconium dichloride (1.81 mmmol) with stirring. In accordance with Method 6, 30.00 g of silica (MS948, 1.6 cc/g P.V., Davison Chemical Co) previously heated to 800° C. under $N_2$ was added to the precursor and stirred. An additional 20.9 g of toluene was added to the mixture and stirring continued with a magnetic stir bar. The initial ratio of liquid volume to total silica pore volume was 1.8. The final ratio of liquid volume to total silica pore volume was 2.1. The mixture was heated at 80° C. for four hours and dried with stirring at reduced pressure (28+ in. Hg vacuum) until it became a free flowing solid, after which stirring was ceased and drying continued at 25° C. for one 16 hour period.

POLYMERIZATION TESTS FOR CATALYSTS

A sample of the catalysts of the invention as prepared above as Catalysts 2-1, 3-1, 3-2, 4-1, 5-1, 5-1A and 6-1 was used for ethylene/1-hexene copolymerization studies as described below. A continuous fluid bed gas-phase reactor operated at 300 psig total pressure was used. A solution of TEAL (1 wt % in isopentane) was fed into the reactor. A detailed composition of ethylene and 1-hexene composition produced is included in Table 1, along with the process data. Polymer samples were collected and analyzed after several bed turnovers.

ating pressure of 75 psi (517 kPa) ethylene (plus solvent vapor pressure). After 30 min the reactor was vented and the contents dumped into a beaker under air and filtered. The data is shown in Table 3.

TABLE 1

| Catalyst | 2-1 | 3-1 | 3-2 | 4-1 | 5-1 | 5-1A | 6-1 |
|---|---|---|---|---|---|---|---|
| PROCESS DATA | | | | | | | |
| H2 conc. (ppm) | 86 | 87 | 86 | 82 | 82 | 83 | |
| C6/C4 conc (mol %) | 0.50 | 0.50 | 0.52 | 0.53 | 0.47 | 0.51 | 0.51 |
| C2 conc. (mol %) | 30.4 | 30.6 | 30.1 | 30.2 | 28.8 | 30.2 | 30.4 |
| H2/C2 Ratio | 2.8 | 2.8 | 2.8 | 2.7 | 2.9 | 2.7 | 2.7 |
| C6/C2 Ratio | 0.016 | 0.016 | 0.017 | 0.017 | 0.016 | 0.017 | 0.017 |
| Reactor Temp (°F.) (°C.) | 156 (69) | 154 (68) | 154 (68) | 154 (68) | 153 (67) | 154 (68) | 154 (68) |
| Productivity (g/g) | 1351 | 1168 | 2044 | 1703 | 2024 | 1210 | 1175 |
| ALKYL TYPE | TEAL | TEAL | TEAL | TEAL | TEAL | TEAL | TEAL |
| POLYMER DATA | | | | | | | |
| Melt Index (MI) (g/10 min) | 1.98 | 2.09 | 1.55 | 1.57 | 2.28 | 1.56 | 1.64 |
| Density (g/cc) | 0.9170 | 0.9162 | 0.9091 | 0.9160 | 0.9169 | 0.9141 | 0.9150 |
| APS (microns) | 511 | 524 | 553 | 511 | 546 | 519 | — |
| % Fines <250 microns | 15.15% | 12.15 | 10.90 | 4.15% | 1.65% | 12.30% | — |
| % Fines <126 microns | 3.75% | 2.55 | 1.70 | 0.75% | 0.20% | 1.30% | — |
| % Fines <63 microns | 0.45% | 0.40 | 0.20 | 0.20% | 0.00% | 0.15% | — |
| Bulk Density (g/cc) | 0.4260 | 0.4560 | 0.4328 | 0.4155% | 0.4160 | 0.4320 | 0.4350 |
| HLMI (g/10 min) | 38.20 | 40.19 | 30.78 | 26.97 | 18.07 | 28.26 | 40.70 |
| % Pore Volume | 60 | 88 | 88 | 180 | 180 | 370 | 210 |

Polymerization of Catalyst 1-1, 1-2, 2-2, 3-3 and 3-4

Catalysts 1-1, 1-2, 2-2, 3-3 and 3-4 were run in a hexane slurry polymerization process, as follows:

A 2 liter reactor was charged with 800 ml hexane, 30 ml hexene-1 and 0.28 mL TEAL (24.8 wt % in heptane). The temperature of the reactor was raised to 70° C. and 0.125 g of each of the catalysts was charged along with sufficient ethylene to raise the total reactor pressure to 150 psig (1136 kPa). Ethylene was fed for 40 minutes and then blocked in. The reactor was cooled and the pressure vented. The hexane slurry of polyethylene was removed from the reactor and the hexane allowed to evaporate. Residual volatiles were removed at 75° C. in vacuo. The polyethylene (PE) powder was weighed. The data is shown in Table 2.

TABLE 2

| Catalyst | Al/Zr | % Pore Volume | PE yield (g) | Productivity (g PE/g Cat) |
|---|---|---|---|---|
| 1-1 | 65:1 | 63 | 71.6 | 572.8 |
| 1-2 | 100:1 | 95 | 72.4 | 579.2 |
| 2-2 | 65:1 | 88 | 84.9 | 679.2 |
| 3-3 | 110:1 | 117 | 65.2 | 521.6 |
| 3-4 | 120:1 | 88 | 68.9 | 551.2 |

Polymerization of Catalysts 5-2, 5-3, 5-4, 5-5 and 5-6

Polymerizations were performed in 400 mL of dry hexane in a nitrogen purged 1 L Zipperclave reactor (Autoclave Engineers) equipped with an external temperature control jacket. In a glove box a charge of the supported catalyst, usually 50 to 200 mg, was loaded into a short length of SS tubing between two ball valves and backed by a small bomb containing 20 mL dry hexane. This device was attached to the reactor under an $N_2$ purge. The cocatalyst (0.200 mL 25 wt % triethylaluminum in heptane) and 45 mL of dry 1-hexene was injected into the reactor and the mixture heated to 60° C. with stirring. Stirring was stopped and the catalyst flushed into the reactor by the hexane backed with 75 psi (517 kPa) ethylene pressure. Stirring was immediately restarted while the reactor reached its regulated oper-

TABLE 3

| Catalyst | Cat. amt. (mg) | Yield (g) | Productivity (g/g) | Activity (g/mmol · atm · h) | % Pore Volume |
|---|---|---|---|---|---|
| 5-2 | 50 | 21.3 | 426 | 2887 | 130 |
| 5-3 | 50 | 24 | 469 | 4359 | 150 |
| 5-4 | 200 | 4.4 | 22 | 199 | 150 |
| 5-5 | 50 | 19.8 | 397 | 2441 | 150 |
| 5-6 | 200 | 2.6 | 13 | 33 | 110 |

Polymerization of Catalysts 1-3, 1-4, 5-7, and 5-8

Polymerizations using Catalysts 1-3, 1-4, 5-7, and 5-8 were carried out according to the method described for the experiments summarized by Table 3. These results are reported in Table 4. Catalysts for which the total pore volume of the precursor solution was less than the pore volume of the support caused fouling on the reactor wall and agitator.

TABLE 4

| Catalyst | Cat. amt. (mg) | Yield (g) | Productivity g/g | Activity gPE/mmol Zr atm hr | % Pore Volume | Fouling |
|---|---|---|---|---|---|---|
| 5-7 | 50 | 21.9 | 438 | 3997 | 178 | No |
| 5-7 | 50 | 21.8 | 436 | 3978 | 178 | No |
| 5-7 | 50 | 23.2 | 464 | 4234 | 178 | No |
| 5-8 | 50 | 19.9 | 398 | 3734 | 134 | No |
| 5-8 | 50 | 21.6 | 432 | 4053 | 134 | No |
| 5-8 | 50 | 19.4 | 388 | 3640 | 134 | No |
| 1-3 | 50 | 22.4 | 448 | 4174 | 91 | Yes |
| 1-3 | 50 | 15.4 | 308 | 2869 | 91 | Yes |
| 1-3 | 50 | 15.8 | 316 | 2944 | 91 | Yes |
| 1-3 | 50 | 13 | 260 | 2422 | 91 | Yes |
| 1-3 | 100 | 35.5 | 355 | 3307 | 91 | Yes |
| 1-3 | 100 | 34.8 | 348 | 3242 | 91 | Yes |
| 1-3 | 100 | 44.2 | 442 | 4118 | 91 | Yes |
| 1-4 | 50 | 14 | 280 | 2608 | 79 | Yes |

TABLE 4-continued

| Catalyst | Cat. amt. (mg) | Yield (g) | Productivity g/g | Activity gPE/mmol Zr atm hr | % Pore Volume | Fouling |
|---|---|---|---|---|---|---|
| 1-4 | 50 | 17.1 | 342 | 3185 | 79 | Yes |
| 1-4 | 50 | 16.8 | 336 | 3129 | 79 | Yes |

While the present invention has been described and illustrated by reference to particular embodiments, it will be appreciated by those of ordinary skill in the art that the invention lends itself to variations not necessarily illustrated herein. For example, it is within the scope of this invention to mix at least two of the catalysts of the invention or to use the catalyst of the invention with any other catalyst or catalyst system known in the art, for example a traditional Ziegler-Natta catalyst or catalyst system. Also the catalyst system of the invention can be used in a single reactor or in a series reactor. For this reason, then, reference should be made solely to the appended claims for purposes of determining the true scope of the present invention.

We claim:

1. A method for forming a supported catalyst system, the method comprising combining porous support having an average particle size in the range of from about 10 μm to 500 μm with one or more solutions of metallocene and activator wherein the total volume of the solution or solutions together is in the range of from less than two times the total pore volume of the porous support to above one times the total pore volume of the porous support; and drying the resulting catalyst system.

2. The method of claim 1 wherein the metallocene solution and the activator solution are combined first before being combined with the porous support.

3. The method of claim 1 wherein one or more metallocene solutions is contacted with the porous support followed by the addition of one or more activator solutions.

4. The method of claim 1 wherein one or more activator solutions is contacted with the porous support first before being contacted with one or more metallocene solutions.

5. The method of claim 1 wherein the metallocene solution comprises two or more metallocene catalyst components.

6. The method of claim 1 wherein the activator solution comprises two or more activators.

7. The method of claim 1 wherein the mole ratio of the metal of the activator to the transition metal of the metallocene catalyst component is in the range of from between 0.3:1 to 800:1.

8. The method of claim 1 further comprising the step of prepolymerizing the supported catalyst system.

9. The method of claim 1 wherein the metallocene solution comprises dimethylsilyl(tetramethylcyclopentadienyl)(adamantylamido)titanium dichloride.

10. A method for forming a supported catalyst system, the method comprising combining a porous support having an average particle size in the range of from about 10 μm to 500 μm and a liquid comprising a metallocene, wherein the total volume of the liquid is in the range of from less than two times the total pore volume of the porous support to above one times the total pore volume of the porous support; and drying the resulting catalyst system.

11. The method of claim 10 wherein the liquid further comprises an activator.

12. The method of claim 10 wherein the method further comprises the additional step of incorporating an activator into said support.

13. The method of claim 12 wherein the incorporating step is conducted prior to the combining step.

14. A catalyst system produced by the method of claim 1.

15. A catalyst system produced by the method of claim 10.

16. A catalyst system produced by the method of claim 2.

17. A process for polymerizing olefins alone or in combination with one or more other olefins, said process comprising polymerizing in the presence of a supported catalyst system prepared by the method of claim 1.

18. A process for polymerizing olefins alone or in combination with one or more other olefins, said process comprising polymerizing in the presence of a supported catalyst system prepared by the method of claim 10.

* * * * *